(12) United States Patent
Meringdal

(10) Patent No.: US 6,474,168 B1
(45) Date of Patent: Nov. 5, 2002

(54) DYNAMIC PRESSURE SENSOR, PHOTO ACOUSTIC GAS DETECTOR, MICROPHONE, HYDROPHONE AND METHOD OF THEIR MANUFACTURE

(75) Inventor: Frode Meringdal, Hagan (NO)

(73) Assignee: Presens AS, Oslo (NO)

( * ) Notice: Subject to any disclaimer, the term of this patent is extended or adjusted under 35 U.S.C. 154(b) by 0 days.

(21) Appl. No.: 09/555,217

(22) PCT Filed: Nov. 25, 1998

(86) PCT No.: PCT/NO98/00346
§ 371 (c)(1),
(2), (4) Date: May 26, 2000

(87) PCT Pub. No.: WO99/30122
PCT Pub. Date: Jun. 17, 1999

(30) Foreign Application Priority Data

Nov. 26, 1997 (NO) ................................................ 975447

(51) Int. Cl.⁷ .................................................. G01L 7/08
(52) U.S. Cl. ...................................... 73/715; 73/861.47
(58) Field of Search ........................ 73/715, 721, 728, 73/705, 861.47, 861.42, 861.63, 31.06, 31.04; 250/344, 345, 346

(56) References Cited

U.S. PATENT DOCUMENTS

| | | | | |
|---|---|---|---|---|
| 4,112,736 A | * | 9/1978 | Wheldon et al. | ............... 73/23 |
| 4,722,227 A | | 2/1988 | Grob et al. | .................... 73/706 |
| 4,771,638 A | * | 9/1988 | Sugiyama et al. | ............. 73/721 |
| 5,259,248 A | | 11/1993 | Ugai et al. | |
| 5,633,552 A | | 5/1997 | Lee et al. | .................... 310/311 |

FOREIGN PATENT DOCUMENTS

| | | | |
|---|---|---|---|
| JP | 1156637 A | * | 6/1989 |
| WO | 98/12522 | | 3/1998 |

* cited by examiner

Primary Examiner—Eric S. McCall
(74) Attorney, Agent, or Firm—Wenderoth, Lind & Ponack, L.L.P.

(57) ABSTRACT

The present invention pertains to a pressure sensor for measuring absolute dynamic pressure. The sensor comprises a frame surrounding a diaphragm, wherein the diaphragm is spaced from the frame by at least two slits which define a restriction that places a reference chamber in fluid communication with a surrounding environment. The diaphragm is connected to the frame at two transition areas, which transition areas are separated from one another by the slits.

21 Claims, 5 Drawing Sheets

Fig. 2a
Fig. 2b
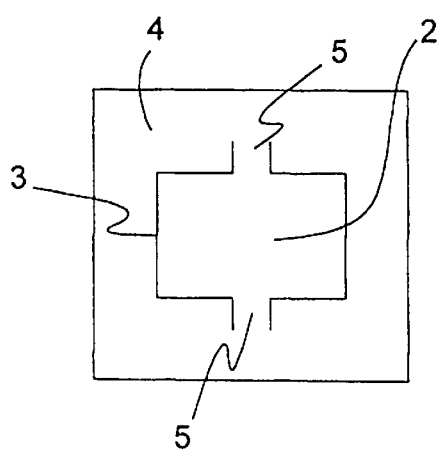
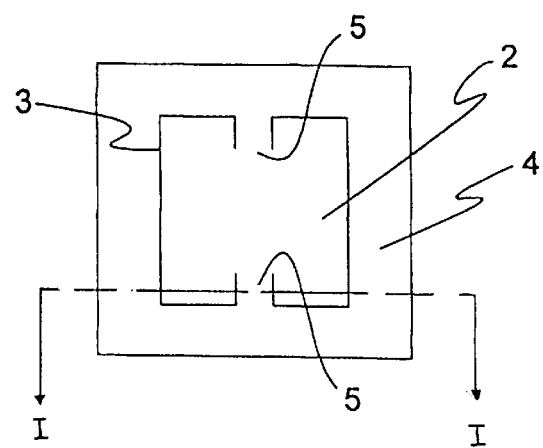

DYNAMIC PRESSURE SENSOR, PHOTO ACOUSTIC GAS DETECTOR, MICROPHONE, HYDROPHONE AND METHOD OF THEIR MANUFACTURE

BACKGROUND OF THE INVENTION

The present invention pertains to a pressure sensor for measuring absolute dynamic pressure, and more particularly, a sensor comprising a frame, a diaphragm arranged in the frame and attached thereto along parts of the outer edge of the diaphragm, where the diaphragm has a measurement side toward the surroundings and a rear side, and further a reference chamber behind the diaphragm rear side and a restriction connecting the reference chamber to the surroundings, as well as a signal-providing element arranged to detect mechanical stress in an attachment part in the outer diaphragm edge. The invention also pertains to a photoacoustical gas detection sensor, a microphone and a hydrophone based upon use of the pressure sensor. Further, the invention pertains to a method for manufacturing a pressure sensor for dynamic absolute pressure, and a method for manufacturing a photoacoustical gas detection sensor.

Pressure sensors based on movement/flexure of a diaphragm are as a starting point only able to measure differential pressures. E.g. in silicon pressure sensors the sensor element consists of a diaphragm which on respective sides thereof is in contact with a fluid under pressure, and which diaphragm flexes dependent on the pressure difference between the fluids.

In order to manufacture an absolute pressure sensor with a differential sensor as a starting point, one has to provide a substantially closed chamber with a reference fluid on one side of the diaphragm. The volume of this chamber is called the reference volume. The reference volume, and consequently the reference pressure, will vary with temperature. Hence, temperature changes will introduce errors in the measurement system.

Another aspect that must be taken into consideration in connection with the reference volume, is that when the diaphragm flexes toward the reference chamber, the fluid in the reference volume will be compressed, and thereby form a pressure, depending on the compressibility of the fluid. This phenomenon is termed pressure feedback, and such pressure feedback affects the sensitivity of the system. In order to minimize the pressure feedback, the reference volume must be large, so that the diaphragm flexing volume constitutes only a small fraction of the reference volume. (Alternatively, the diaphragm must be rigid, and this means at the same time low sensitivity.)

One way of overcoming the two above mentioned problems of temperature errors and pressure feedback, is to arrange a reference chamber with a vacuum behind the diaphragm. A temperature increase will then not give any increase of pressure in the reference chamber, and pressure feedback cannot arise. However, such an embodiment with a vacuum in the reference volume, will lead to limitations in the pressure values that can be measured. If the static pressure is approximately 1 bar, as will normally be the case in the surroundings, the diaphragm must be dimensioned to withstand a pressure difference of 1 bar if a vacuum is used in the reference volume, and such a diaphragm will be rather poorly suited for measuring very small pressures, in particular dynamic pressures e.g. in connection with acoustical oscillations. When these small, dynamic pressures are to be measured, the diaphragms must be dimensioned in relation thereto, and a static pressure difference of e.g. 1 bar will then possibly lead to destruction of such a diaphragm. In other words, in connection with measuring dynamic pressures having small pressure values, e.g. in the 1 pascal range, one must use a reference volume that contains a fluid.

The sensitivity of the measurement system will also depend on the volume displacement of the diaphragm. The volume displacement is flexure volume per pressure unit, i.e. the volume occupied by the flexed diaphragm in the reference chamber, divided by the pressure. In general, a good sensitivity implies a large flexure/volume displacement. This can easily be appreciated by considering a very thin diaphragm that flexes easily when a pressure differential is present. The disadvantage of a large volume displacement is that the pressure feedback increases, and the sensitivity of the sensor is reduced.

If it is desirable to measure rapidly changing, dynamic pressures, typically in connection with sound oscillations, it is possible to make a small channel into the reference chamber, thus letting the surrounding medium into the chamber. At the outset this will make the diaphragm more robust to exposure to atmospheric pressure, temperature changes, or to handling. Such a channel or opening that connects the reference volume to the sensor surroundings, or more generally to the pressure input of the sensor, is called a restriction. This is because the opening/channel is so narrow that it will take a long time until the pressure inside the reference volume is equalized in relation to the external pressure. The restriction has the effect of a negative feedback regarding slow changes, i.e. low frequencies in the pressure oscillations. The cross section area and the length of the restriction represent a flow resistance, equivalent to an electrical resistance, and the reference volume multiplied by the fluid compressibility, represents a reservoir, equivalent to an electrical capacity, and together the restriction and the reference chamber then operate as a first order lowpass filter for the pressure oscillations, since the low frequencies have sufficient time to get through the restriction and thereby influence both sides of the diaphragm, while the high frequencies will merely affect the diaphragm side facing the surroundings/the pressure input, and therefore will be measurable. In other words, the sensor will be sensitive to frequencies higher than the corner frequency of this filter. By shaping the restriction and the reference chamber in a suitable manner, it is possible to control the corner frequency of the filter, and in this way the measuring range of the sensor. If it is desirable to achieve an extended measuring range down toward low frequencies, then a large reference volume will be advantageous, since this provides a low corner frequency.

However, size is often an important criterion in manufacturing a sensor that fulfils requirements set by an application. In order to make a small sensor, it is of course important that the reference volume is made as small as possible, but with a small reference volume, and when it is desirable to measure relatively low frequencies, one must prepare a very narrow restriction, and the diaphragm must give an extremely small volume displacement. Also if it is desirable to manufacture pressure sensors in planar technology, i.e. in batches, the size of the reference volume should be restricted. The advantage of this type of manufacturing is that the sensors can then be manufactured at a reasonable cost.

The most common application regarding measurement of dynamic pressures, is in sound measurement, which comprises dynamic pressures all the way down into the $\mu$Pa range. When it is desirable to make measurements in these pressure ranges, static pressure variations are quite destructive. Variations due to high and low pressures may amount to several tens of kilopascals (1 kPa=10 mBar). If one wishes to measure dynamic pressures under water at various depths, the static pressure changes may be even much larger. When dynamic pressures shall be measured, one will often use sensor elements that are sensitive only to dynamic pressure, and the most common example of such a sensor element is a piezoelectric crystal. Such crystals have many good characteristics, inter alia a low price, a high natural frequency and a low sensitivity to acceleration. However, it is a disadvantage that such piezoelectric crystals have a limited stability over time, as well as poor low frequency characteristics (in comparison with monocrystalline piezoresistive structures).

Therefore, one has lately to an increasing degree changed to using diaphragm sensors made by silicon, which material exhibits better stability. Embodiments of such diaphragm sensors have been mentioned above. One has tried to manufacture diaphragm sensors with restrictions in order to provide a high sensitivity, and by means of cost reasonable manufacturing technologies. For instance Norwegian patent application no. 97.1201 discloses a pressure sensor based on solid state technology, where e.g. a semiconductor chip, preferably with silicon as a start material, is processed to comprise a relatively thick frame, an intermediate, thin diaphragm and a central, thick block that can be pushed down by an overpressure, a reference chamber being provided underneath the block and diaphragm, between the semiconductor chip and a substrate thereunder, e.g. a glass substrate. At least two rigid and thick beam connections between the central block and the surrounding frame provide areas where high mechanical stresses are induced when the block exhibits a deflection due to a pressure variation, and signal-providing piezoresistive elements are located in these areas, which in their turn are located where the beams pass on to the frame and the block respectively. Pressure sensors of this type can be batch manufactured from a larger semiconductor wafer that is bonded to a larger substrate disc, then to be cut into single sensors in the end. This previously known pressure sensor can also be equipped with a restriction to provide a connection between the reference chamber and the sensor pressure input, so that a suitable corner frequency can be provided for the low end of the frequency measuring range. However, this known sensor has disadvantages like a large area and a significant volume displacement due to the thin diaphragm areas, and these features do not contribute to the sensitivity. Besides, the manufacturing process is relatively complicated and costly, and a sensor with a closed reference chamber is not very suitable for batch production.

Norwegian patent no. 300,078 discloses a photoacoustical gas detector having a chamber that contains a gas type to be detected somewhere else. The chamber has been manufactured by bonding together two silicon or quartz plate elements prepared by the use of planar technology. The chamber has windows for transmission of pulsed IR radiation, and a pressure sensor with a diaphragm is arranged above a closed space that communicates with the chamber. However, this gas detector exhibits clear limitations regarding practical implementation and manufacturing costs. The location of a signal-providing element in relation to the diaphragm, in order to achieve high sensitivity, is not mentioned in the patent. Nor are any restrictions between a measurement chamber and a reference chamber mentioned in that publication.

U.S. Pat. No. 5,633,552 discloses a pressure sensor which comprises a chamber and a slab attached to a frame lying on top of the chamber. The slab is attached to the frame along one of the sides, and constitutes sort of a cantilever beam from the frame. The remaining three sides of the slab are separated from the frame by a vertical slit. A piezoelectric element is placed on the slab in the area where it is attached to the frame. The slit width is approximately 10 $\mu$m. This device has a high sensitivity (2 mV/$\mu$Bar for frequencies situated in the range 100–1000 Hz), the slab being easily movable by means of small pressure differences. In order to maintain the slab flat in the resting position, it is manufactured in the form of three sandwiched layers having different internal stresses. The device has a relatively large volume displacement, and therefore large pressure feedback. In addition thereto, the use of a piezoelectric element for measuring mechanical stress will lead to unstable measurements, since a piezoelectric element is not as stable over time and with regard to temperature, as e.g. a piezoresistive element. The sensor indicated in the publication must be provided with a relatively large reference chamber in order to compensate for the effect of the large volume displacement. This makes batch manufacturing of the complete sensor very difficult. The top part of the sensor, i.e. the sides and roof (slab) of the reference chamber are batch manufactured as parts of a larger wafer, but thereafter the wafer, including chamber sides and slabs, is cut into a plurality of top parts, and each respective top part is laminated to a bottom. This manufacturing method is costly and not very efficient.

The purpose of the present invention is in a first aspect to provide a pressure sensor for measuring absolute, dynamic pressure, which sensor satisfies high sensitivity requirements, and which sensor is provided with a small reference chamber, and furthermore, it can be manufactured in planar technology to provide a reasonable manufacturing cost. Other aspects of the invention will appear below.

SUMMARY OF THE INVENTION

In accordance with the present invention, the purpose is achieved by a pressure sensor of the type indicated in the introduction, and which is characterized in that the diaphragm is attached to the frame along at least two parts of the outer diaphragm edge, at least one of the diaphragm attachment parts comprising an area where mechanical stresses caused by the pressure, are concentrated, the signal-providing element being arranged in this area, and that remaining parts of the outer edge of the diaphragm are separated from the frame by slits constituting the restriction.

In an important embodiment, the diaphragm and the frame are in one piece formed from a planar material disk, the slits then being slits all the way through the disk thickness, said area then being a transition area from the diaphragm to the frame.

The measurement side of the diaphragm is preferably in the same plane as the adjacent surface of the frame.

In a preferred embodiment, the material disk is of silicon, and the signal-providing element is then preferably a monocrystalline piezoresistive element.

In a further preferred embodiment, the slits that as a starting point have a depth dimension substantially transverse to the measuring side of the diaphragm, continue in under the rear side of the diaphragm, the frame or the wall of the reference chamber being shaped with a shoulder closely adjacent the rear side of the diaphragm in an area along the diaphragm edge.

Preferably, the dimensions of the restriction are adapted to provide a flow resistance that together with the volume of the reference chamber constitutes a low pass filter for the pressure equalising rate of the sensor, said filter having a corner frequency adapted to the frequency range of the dynamic pressure variations to be measured.

Several diaphragm attachment parts may be formed, arranged with intervals along the outer edge of the diaphragm, and these attachment parts will comprise stress concentration areas, as mentioned above.

Preferably, the sensor comprises at least one piezoresistive element incorporated into said area or said areas, as a signal-providing element, preferably as an element in bulk material or as a thin film element on the surface.

In another aspect of the invention, there is provided a photoacoustical gas detection sensor for detection and/or concentration determination of a particular gas in the surroundings of the sensor, wherein the sensor comprises a measurement chamber filled with the gas in question, a radiation source spaced from the measurement chamber, and inside or adjacent to the measurement chamber a pressure sensor for measuring absolute dynamic pressure in the measurement chamber. The measurement chamber is equipped with at least one wall area or window that is transparent to radiation from the source with a wavelength that can be absorbed or scattered by the gas to be detected. The pressure sensor comprises a frame, a diaphragm arranged in the frame and attached thereto by the outer diaphragm edge, said diaphragm having a measurement side toward the measurement chamber and a rear side. Further, the pressure sensor comprises a reference chamber that substantially is not exposed to radiation, behind the rear side of the diaphragm, and a restriction connecting the reference chamber to the measurement chamber, and a signal-providing element arranged to detect mechanical stress in an attachment part at the outer diaphragm edge. The gas detection sensor is characterized in that the diaphragm is attached to the frame along at least two parts of the outer diaphragm edge, at least one of the attachment parts of the diaphragm comprising an area in which mechanical stresses caused by the pressure, are concentrated, and that remaining parts of the outer edge of the diaphragm are separated from the frame by slits constituting the restriction, the reference chamber and the measurement chamber constituting together a closed system filled by the same gas.

The measurement chamber and the reference chamber of the gas detection sensor are manufactured by laminating and etching techniques and with substantially similar dimensions on respective sides of the frame with the diaphragm and the slits, in order to constitute a compact unit.

In a preferable embodiment of the gas detection sensor in accordance with the invention, the diaphragm has a light reflecting coating on one of its sides, a wall area of the measurement chamber opposite to the diaphragm then having a light transparent area/window.

In a further aspect of the invention, there is provided a microphone comprising a pressure sensor for measuring absolute dynamic pressure, a microphone housing and signal wires, and the microphone is characterized in that the pressure sensor is of the type indicated in the first aspect of the invention.

In a further aspect of the invention, there is provided a hydrophone comprising a pressure sensor for measuring absolute dynamic pressure, a hydrophone housing and signal wires, and the hydrophone in accordance with the invention is characterized in that the pressure sensor is of the type indicated in the above first aspect of the invention.

A further aspect of the invention comprises a method for manufacturing a pressure sensor for dynamic absolute pressure, of the type indicated in the first aspect of the invention, and wherein the diaphragm and the frame are in one piece formed from a plane material disk, the slits then being slits all the way through the disk thickness, so that the mentioned area is then a transition area from the diaphragm to the frame. The method in accordance with the invention is characterized in that in a first, thin disk, preferably of silicon, a restriction is provided in the form of at least two elongate, narrow slits, preferably by means of ionic etching, said restriction defining a diaphragm in relation to a surrounding frame in that the restriction substantially surrounds the outer edge of the diaphragm, except along transition areas from the diaphragm to the frame, that in a second material disk, preferably of silicon, a recess is etched out, e.g. by wet etching, and that the two disks are laminated to each other so that the recess constitutes a reference chamber behind the diaphragm, and so that the restriction leads into the reference chamber.

In a first embodiment of the method, the second material disk, prior to laminating to the first disk, is exposed to a further etching step with precise forming of a step along the upper edge of the recess, in such a position that when the laminating is made, the restriction is provided with a bent extension in behind the diaphragm.

In a second embodiment of the method, a third material layer is provided between the two disks by depositing a thin film on to one of the disks, by growing e.g. an oxide on one of the disks or by laminating a third material disk to one of the disks, with an opening adapted to and not smaller than the opening in the frame, and thereafter the remaining one of the two disks is laminated to the disk having the third material layer, so that the restriction is provided with a bent extension in behind the diaphragm by means of the third material layer and the edge of the second disk around the recess.

In a third embodiment of the method in accordance with the invention, the first material disk, prior to laminating to the second disk, is exposed to a further etching step on its rear side, at least in an area around the rear side opening of the restriction, in order to provide the restriction with a bent extension in behind the diaphragm when the laminating is made.

In a favorable embodiment of the method, a number of sensors are batch manufactured by preparing a number of first disks simultaneously and next to each other on a first, larger material disk, a number of second disks are prepared in a corresponding manner next to each other on a second, larger material disk, the two larger material disks are laminated to each other, and single sensors are then provided by sectioning the bonded, larger disks.

In a further aspect of the invention there is provided a method for producing a photoacoustical gas detection sensor of the type indicated according to the second aspect of the invention, and this method is characterized in that in a first disk, preferably of silicon, a restriction is provided having the shape of at least two elongate, narrow slits, preferably by means of ionic etching, said restriction defining a diaphragm in relation to a surrounding frame in that the restriction substantially surrounds the outer edge of the diaphragm, except along transition areas from the diaphragm to the frame, that in a second disk, preferably of silicon, a first recess is provided, e.g. by machining or wet etching, that the two disks are laminated to each other in order that the first recess shall constitute a measurement chamber in front of the diaphragm, and in such a manner that the restriction leads into the measurement chamber, that in a third disk, preferably of glass, there is provided a second recess, e.g. by machining or wet etching, and that the third disk is laminated to the first disk in an atmosphere of a predetermined gas in such a manner that the second recess constitutes a reference chamber behind the diaphragm, whereby the restriction also leads into the reference chamber and thereby constitutes a channel between the measurement chamber and the reference chamber, which chambers will both contain this gas after the lamination.

In a favorable embodiment of the method for producing a photoacoustical gas detection sensor, the second disk is provided with a through hole, e.g. by machining, and a fourth disk that is transparent to light which excites the gas in the measurement chamber, is laminated to the second disk to cover the hole.

In a further favorable embodiment, a number of gas detection sensors are batch manufactured by preparing groups of the first, second, third and possibly fourth disks respectively as parts of larger first, second, third and possibly fourth material disks respectively, the respective larger material disks are laminated to each other, possibly in an atmosphere of a certain gas that is to be detected, and single gas detection sensors are then provided by dividing the bonded larger disks.

BRIEF DESCRIPTION OF THE DRAWINGS

In the following, the invention shall be described in further detail with reference to exemplary embodiments, and with reference to the appended drawings, where FIG. 2a and FIG. 2b show two possible embodiments of the diaphragm in the sensor in accordance with the invention.

DESCRIPTION OF THE PREFERRED EMBODIMENTS

Figure 1:
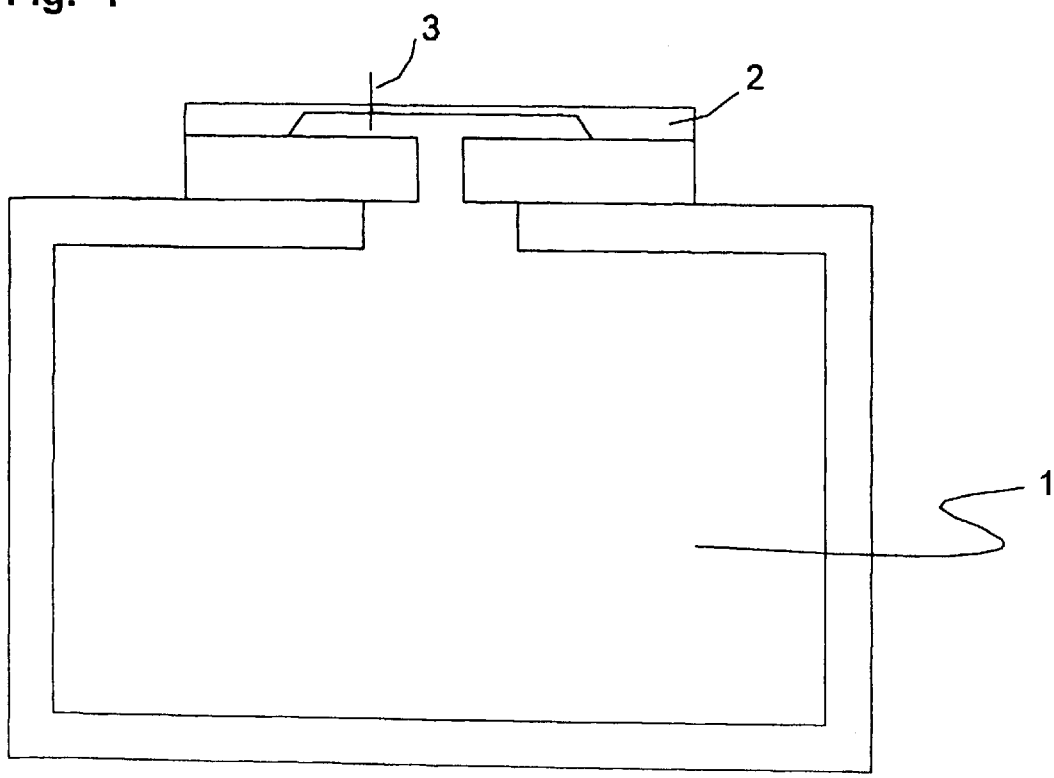
FIG. 1 shows schematically a general pressure sensor for absolute pressure.

In FIG. 1 appears an absolute pressure sensor according to the prior art. The sensor comprises a reference chamber 1, a sensor diaphragm 2 and a restriction 3. In the shown embodiment the restriction consists simply of openings in diaphragm 2. Because of the restriction 3, the reference chamber 1 will, as previously mentioned, necessarily contain the same gas as the surroundings, and have the same static pressure as the surroundings. For dynamic pressures with oscillation frequencies higher than a typical corner frequency determined by the restriction 3 and characteristics of the gas inside the chamber 1, the diaphragm will exhibit a useful sensitivity, and a measurement signal can be achieved from the sensor, using a signal-providing element associated with the diaphragm for measuring the deflection thereof, or possibly via some other parameter associated with the deflection.

A fundamental quality of diaphragm sensors is that the sensitivity is dependent on the volume displacement. The simplest manner for visualizing this effect, is to consider the energy that is introduced into the elastic diaphragm when it is affected by a pressure. For a given pressure, the work done by the pressure, is equal to W=PV, where V is the diaphragm volume displacement. This must be the same energy that is stored in the mechanical stresses in the diaphragm (a very small energy storage in compressing the inside fluid is here disregarded), given by the expression $W=\int\int\int_v \sigma^{dv}/2E$, where v is the volume of material (e.g. silicon crystal) containing the stresses, E is the modulus of elasticity of the material and σ is the mechanical stress. One can see here that if sensitivity shall be increased without increasing the volume displacement, the stresses must be concentrated within a diaphragm area that is as small as possible.

As regards the diaphragm in a sensor in accordance with the invention, one utilizes just the feature of concentrating stresses within a small area of the diaphragm, and more specifically, this is done by providing limited connection areas between the diaphragm and the frame surrounding the diaphragm. This feature then leads to high sensitivity, even when using a small reference volume.

In FIG. 2a is shown an embodiment of the diaphragm in a sensor in accordance with the invention. The diaphragm 2 is viewed "from above", i.e. in the direction in which pressure works against the diaphragm surface. The restriction 3 is shaped as two slits all the way through the material which initially forms a complete and connected chip, which however by means of the slits 3 is separated into a surrounding frame 4 and the diaphragm 2. The diaphragm is only attached to the frame at transition areas 5 such that the transition areas 5 serve as attachment structures that connect the diaphragm 2 to the frame 4. The mechanical stresses caused by the pressure on the diaphragm 2, are concentrated in these transition areas.

In FIG. 2b appears a different configuration, however the respective reference numerals refer to corresponding details as in FIG. 2a. A corresponding concentration of stresses is achieved also in this case, in the areas having reference numeral 5.

Figure 3:
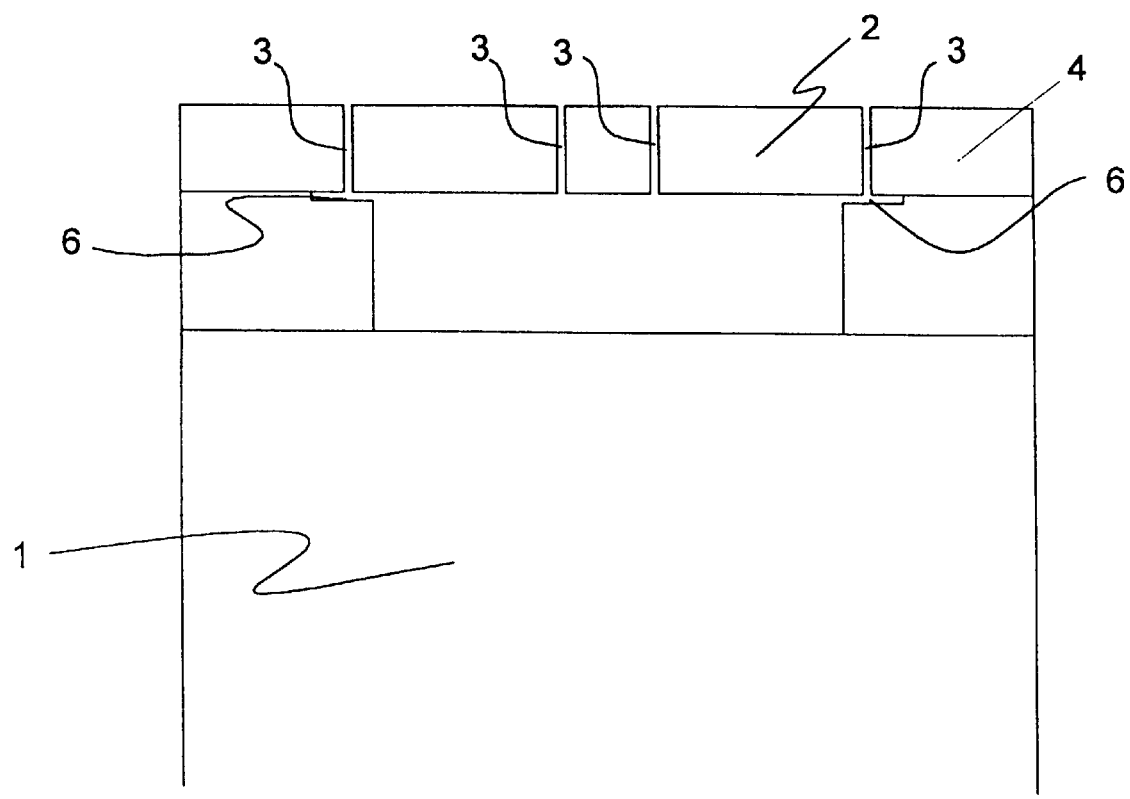
FIG. 3 shows a section through the embodiment appearing in FIG. 2b.

In FIG. 3 appears a section through the sensor shown schematically in FIG. 2b, indicated by means of a broken line. In FIG. 3 appears in particular an embodiment with an extension of the restriction 3, in the form of an extended channel 6 that is bent in under the diaphragm 2. The purpose of this restriction extension is to provide a further possibility for regulating down the corner frequency of the filter. This solution is provided to give a sufficiently large flow resistance when the fluid is a gas. It is a fact that it is not certain that the present technology is able to produce sufficiently narrow slits directly, and an extension of the restriction such as shown in FIG. 3, will then possibly remedy this.

Of course, other geometries for such slits 3 that are an essential feature of the invention, can be provided. The geometries shown in FIG. 2a and FIG. 2b are only examples. The important point is the combination of a restriction and a concentration of stresses in a small area. Etching of thin slits all the way through the material chip, thereby to provide a diaphragm, will then give just the desired combination. The system will operate approximately like a piston that is fastened by means of a few small springs.

Regarding the embodiment shown in FIG. 3, it is to be noted that also the geometry as viewed in a section through the diaphragm and underlying layers, will be variable within the inventive framework. The material chip constituting the top, i.e. the diaphragm and the frame, needs e.g. not have the same thickness all over, see for instance FIG. 5. The shaping of the reference chamber 1 can be made in several ways, and there are also different manners for providing the extra extension of the restriction.

In one embodiment the diaphragm may be equipped with several areas for stress concentration, i.e. areas where the diaphragm is attached to the frame. This configuration gives a more stable sensor, and diminishes the volume displacement.

If the restriction or slits 3 are shaped to be very narrow, i.e. narrow in relation to the height of the restriction (which height in turn corresponds to the thickness of the diaphragm), one enables achievement of good flow resistance characteristics, and consequently a low corner frequency, which is desirable. With dry etch techniques like e.g. RIE (Reactive Ion Etching) and ICP (Inductively Coupled Plasma), it is possible to etch narrow slits all the way through silicon diaphragms. Even with a silicon diaphragm as thin as 50 μm, it will be possible with this type of etching to provide slits 3 which in the section shown in FIG. 3 will have a height to width ratio of 30:1.

Noting that the idea in its most general form is not limited to planar technology or use of silicon as main material in diaphragm, frame and possible underlying layers, it is remarked that silicon planar technology can be used to manufacture sensors in an efficient and reasonable manner. In this type of technology it is e.g. possible to produce sensors that can do with a reference volume as small as e.g. 800 μm×3,5 mm×3,5 mm, which is a volume that can be implemented in a simple manner with planar technology. Thus, the sensor can be batch manufactured. To compensate for the small reference volume, the volume displacement is limited correspondingly (for instance to $10^{-14}$ m$^3$/Pa or less).

As previously mentioned, an extended channel 6 can be made, which channel is parallel to the diaphragm 2 and is connected to the lower end of the slits 3, i.e. the end closest to the reference chamber 1. This additional channel 6 can be provided by e.g. fixing another silicon chip by laminating, in which other silicon chip there has been processed, e.g. etched, a step in the surface thereof in advance. Such step can be made small and precise, maybe with a dimension smaller than 0.1 μm, and with a variation less than 0.01 μm. Other ways of providing the extended channel shall be mentioned later. Using the extended channel 6, i.e. an extension of the restriction 3, corner frequencies as low as 1 Hz can be achieved, and consequently, measuring ranges can be achieved that are wider than the measuring ranges in the prior art solutions.

The sensor of the invention also comprises a signal-providing element, and in a favorable embodiment of the invention one uses a piezorsistive element that is incorporated into the diaphragm, or more particularly into the transition area 5 between the diaphragm 2 and the frame 4, viz in a position where the mechanical stresses are at their highest. Such piezoresistive elements can be made within the framework of planar technology, and therefore are favorable signal-providing elements. A piezoresistive Wheatstone measuring bridge provides the opportunity for coherent detection of dynamic pressure. This is because the signal from the measuring bridge is the product of the pressure and the feed voltage.

"Planar technology" is here intended to mean a manufacturing technology known from semiconductor manufacture, one may mention epitaxial growth, vapor deposition, sputtering, photolithographic techniques using masking and etching, oxidation processes, diffusion processes as well as micromachining techniques like wet etching, dry etching, wafer laminating etc., all well known techniques which do not need more detailed mention herein.

An obvious use for a sensor in accordance with the invention, is in microphones, and an aspect of the idea relates to just a microphone where a sensor of the type mentioned constitutes the central element. With a suitable microphone housing and necessary wire connections, the microphone is complete, and further description of a microphone in accordance with this invention, is not necessary. Low frequency limitation of the microphone is given by the parameters mentioned above.

Correspondingly, one may manufacture a hydrophone in accordance with the invention, using corresponding considerations as for a microphone. However, in the hydrophone case it is not very probable that sensors are batch manufactured, because the compressibility of liquids is too low, and therefore it is necessary to use a larger reference volume.

Figure 4:
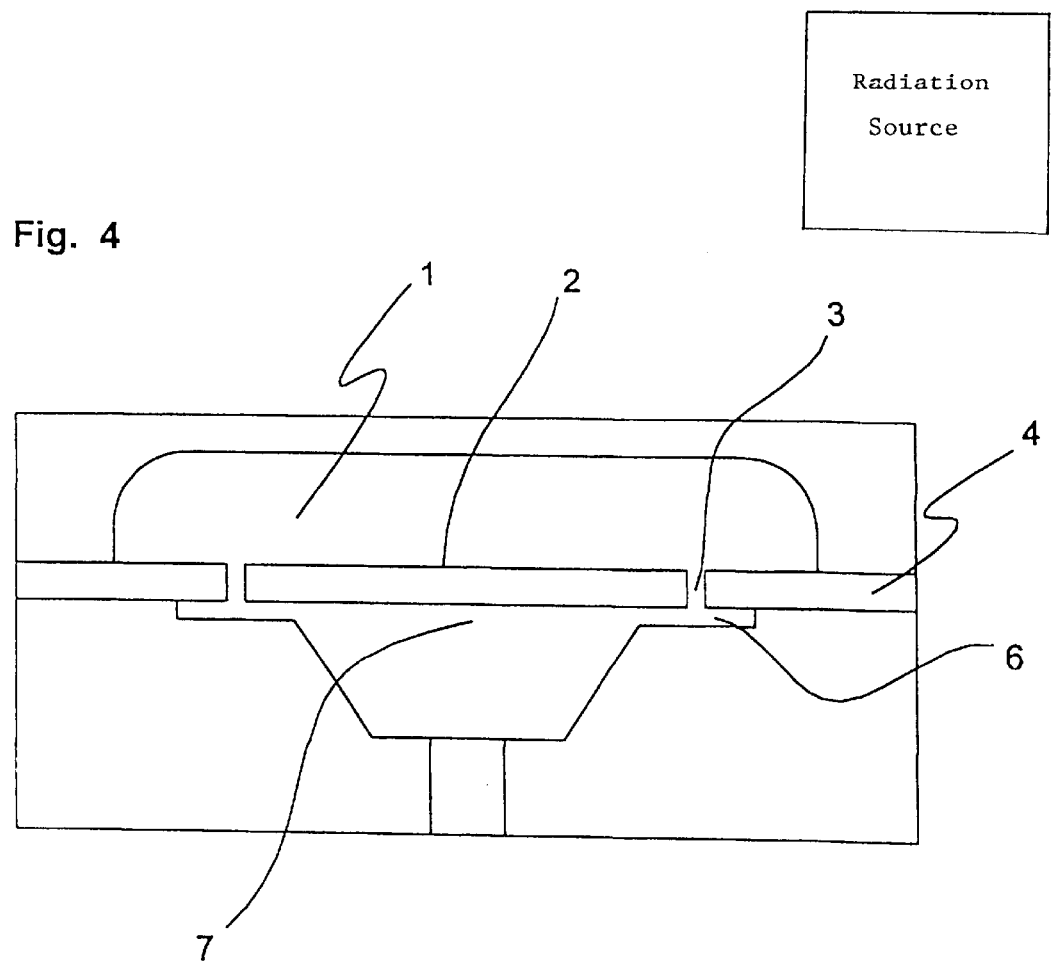
FIG. 4 shows an embodiment of a gas detection sensor in accordance with the invention.

FIG. 4 shows an embodiment of a photoacoustical gas sensor in accordance with the second aspect of the invention. One can see that the difference in relation to what is shown in FIG. 3, is essentially that chambers 1 and 7 are formed both on top and on the underside of the diaphragm 2, so that the diaphragm 2 constitutes a division between a reference chamber 1 and a measurement chamber 7. The two chambers 1 and 7 contain a special gas, and the gas sensor is then adapted to detect or measure the pressure of such a gas in the surroundings or in another volume. A radiation source is used for irradiation of the surroundings or the volume to be investigated, with a wide spectrum of wavelengths that contain strong absorption lines for the gas in question. The measurement chamber 7 is arranged so that the radiation enters the measurement chamber after transmission through the volume to be measured. The disc/chip that defines the reference chamber 1, may well be constituted of glass, in order that the laminating technique shall be compatible with metallized discs/chips and filling of most gas types. Glass is not transparent to radiation that typically excites gases (infrared radiation), and therefore cannot be used for the measurement chamber. Silicon is however transparent to a plurality of wave-lengths that can excite gases, but not to all such wavelengths. For certain gases, e.g. germanium may constitute a better window. If no gas of the type in question is present in the volume to be investigated, the radiation will pass unhindered, enter the measurement chamber 7 and heat the gas in the measurement chamber, because just this wavelength is absorbed by this gas. Using pulsing of the radiation from the radiation source, pressure oscillations will arise in the chamber 7, and the diaphragm 2 will pick up these oscillations.

If the gas in question is found in the investigation area, part of the radiation will be absorbed and scattered, less radiation will reach the measurement chamber 7, and the influence on the diaphragm 2 will be weaker. Thereby, a weaker sound signal is obtained from the gas sensor.

In a favorable embodiment of such a photoacoustical gas sensor, the diaphragm 2 comprises a light reflecting coating, whereby the light transmission in the chamber is doubled, which provides an increased sensitivity, and furthermore it is ensured that light does not enter the reference chamber 1.

One sees that in principle reference chamber 1 and measurement chamber 7 might equally well be interchanged as to their function since the restriction 3 and extended channel 6 work regardless of which chamber constitutes the reference chamber and the measurement chamber. Thus, if the volumes of chambers 1 and 7 are of the same size, either one of these chambers can function as the measurement chamber or the reference chamber. Which materials are used on the different sides of the diaphragm, is then also connected with which gases shall be investigated, and which wavelengths are suitable for special gases.

It is to be noted that the gas sensor can be changed into a pressure sensor such as mentioned above, by providing an opening to the surroundings as indicated e.g. in broken lines right below measurement chamber 7.

Figure 5:
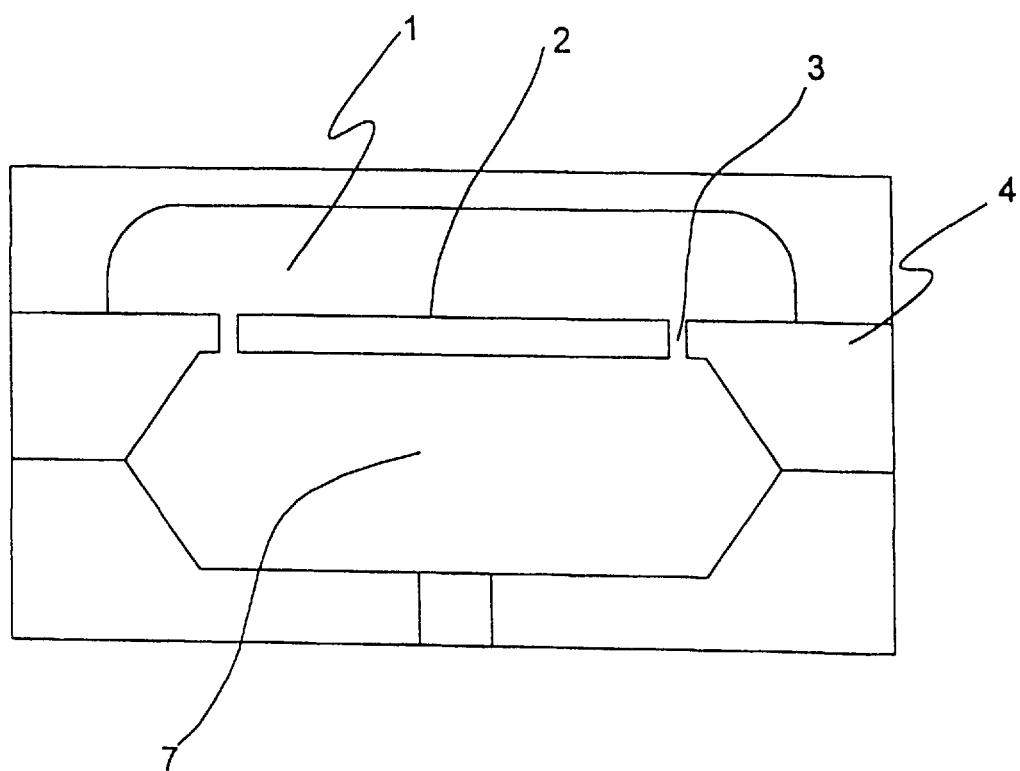
FIG. 5 shows an alternative embodiment of a gas detection sensor.

In FIG. 5 is shown an alternative embodiment of a photoacoustical gas sensor in accordance with the invention. The same reference numerals are used for the same parts as in FIG. 4, it can be noted that the lower laminated silicon layer that provides a measurement chamber 7 together with a relatively thick, upper silicon layer, equally well can be replaced by e.g. a layer of germanium or some other suitable material. In the embodiment shown it appears that the diaphragm 2 itself is etched down to a quite different thickness from the starting material wafer that constitutes the frame 4 outside the diaphragm 2. (Etching down the starting material wafer/chip enables larger flexibility regarding choice of diaphragm thickness. Generally one does not wish to limit diaphragm thickness to standard starting material thickness in low cost applications.) For the rest, in this embodiment one sees that no horizontal restriction part such as shown with reference numeral 6, in FIG. 4, has been used.

In order to change the gas sensor shown here into a pressure sensor, it is possible either to make an opening as shown in broken lines at the bottom, or the complete lower silicon layer can be removed.

When a pressure sensor in accordance with the invention shall be manufactured by means of planar technology, initially a first, thin disc is provided, preferably from silicon. By means of ionic etching or another corresponding technique, the restriction 3 mentioned above is provided in order to define a diaphragm in relation to a surrounding frame in the initial disc/wafer/chip. In a second material disc, also preferably made from silicon, however not limited thereto, a recess is made, e.g. by wet etching or machining, and thereafter the two discs are laminated to each other so that the recess in the second material disc constitutes a chamber behind the diaphragm, and so that the restriction leads into the chamber. This chamber will constitute the reference chamber of the sensor.

In a preferred embodiment of the invention, a transverse extension of the restriction shall be provided on the underside of the diaphragm. One way of doing this has already been mentioned, namely an additional etching step along the upper edge of the recess that is formed in the second material disc, so as to form thereby a bent extension such as shown by reference numeral 6 in FIG. 3, when the two material discs are laminated together.

"Laminating" is in this case intended to comprise techniques for bonding discs together. For silicon this concerns e.g. field-assisted laminating, thermal laminating, eutectical laminating (soldering), gluing etc.

An alternative way of forming a corresponding restriction extension 6 is by providing a third material layer between the two discs.

This may take place by depositing a thin film on one of the two material discs, growing an oxide on one of the discs, or laminating a third material disc to one of the discs. Regardless, the third material layer must be formed with an opening that is adapted to and not smaller than the opening in the frame. The remaining one of the two discs is thereafter laminated to the disc that has received the third material layer, and thereby the desired restriction extension 6, is obtained in behind the diaphragm by means of the third material layer and the edge of the second disk around the recess.

In a third, alternative method the first material disc is exposed to a further etching step on its rear side/underside, prior to laminating to the second disc, at least in an area surrounding the rear side opening of the restriction in the diaphragm. This also results in a bent restriction extension in behind the diaphragm when laminating is made between the first and the second material discs.

When using planar technology, the reduced dimensions allow, if desirable, that a large group of sensors are batch produced, i.e. the etching processes, laminating processes etc. are executed on larger material wafers that comprise many areas that are processed to be sensor elements. When the wafers finally are laminated together, single sensors can be sawn or broken apart. Such a manufacturing technique leads to low production costs.

Regarding manufacturing photoacoustical gas sensors, corresponding techniques as just mentioned, are used, but in this case an additional layer shall also be laminated to the opposite side of the diaphragm/frame, for providing a measurement chamber. In this connection, gas filling of both chambers (measurement chamber and reference chamber) is effected at the same time during laminating the last disc, which laminating has the consequence of closing the system. This last lamination should preferably be borosilicate glass against silicon, so that field-assisted laminating is possible. Field-assisted laminating is made at a relatively low temperature, and will be unproblematic for most gases. Furthermore, it is to be noted that the third disc (in essence after the first disc which defines diaphragm and frame, and the second disc that defines a measurement chamber) has the function of defining a reference chamber, and is provided with a special recess by means of machining or wet etching, before the above mentioned laminating in an atmosphere of the predetermined gas. The third disc may preferably be constituted of glass, or at least of a material that is opaque to the light wavelength in question. The disc that defines a measurement chamber may possibly be provided with a hole, whereafter an additional disc that is transparent to light that excites the gas in the chamber, is laminated to the disc with the hole in order to cover the hole, whereby light can enter the chamber as desired.

In a corresponding manner as in the batch manufacture of pressure sensors, also photoacoustical gas sensors in accordance with the invention can be batch manufactured.

The disclosed embodiments have been described in order to explain various aspects of the invention, but shall not be regarded to limit the invention in any way. As mentioned, sensors can be provided where all diaphragm edges have stress concentration areas, or sensors where an edge may have two or more stress concentration areas. The materials that are used, are not restricted to the ones that have been mentioned. Numerous semiconductor materials can be used in planar technology, and also other materials may be used.

As previously mentioned, the reference chamber and the measurement chamber in a gas detection sensor can be interchanged, and restriction extensions can be provided both "above" and "below" the diaphragm. The diaphragm may have the same thickness as the material disk it constitutes part of, or it may be etched down to another thickness. Substrate disks providing the reference chamber, can be produced using one single disk, or disks laminated together in several layers. Light reflecting layers on a diaphragm may be located on any side of the diaphragm. The slits 3 do not need to be "perpendicularly" cut through the diaphragm/frame, but may equally well exhibit a bent/angled shape, as seen in a cross section like FIG. 3.

What is claimed is:

1. A pressure sensor for measuring absolute dynamic pressure, comprising:

a frame;

a reference chamber;

a diaphragm attached to said frame, with said diaphragm comprising a thin planar structure having an outer edge, a measurement side that is to face a surrounding environment, and a rear side facing said reference chamber;

a first attachment structure interconnecting said frame and a first section of said outer edge of said diaphragm;

a second attachment structure interconnecting said frame and a second section of said outer edge of said diaphragm;

a restriction that is to interconnect said reference chamber and the surrounding environment such that said reference chamber is in fluid communication with the surrounding environment; and a signal-generating element to detect mechanical stress in at least one of said first attachment structure and said second attachment structure, wherein at least one of said first attachment structure and said second attachment structure provides a reduced area where mechanical stresses caused by pressure are concentrated, and said signal-generating element is arranged at said reduced area, and wherein sections of said outer edge of said diaphragm other than said first section and said second section are separated from said frame by slits, with a combination of said slits constituting said restriction.

2. The pressure sensor according to claim 1, wherein said frame and said diaphragm are formed from a single sheet of material, said slits extend completely through said sheet of material, and said reduced area comprises an area of said sheet of material that transitions from said diaphragm to said frame.

3. The pressure sensor according to claim 1, wherein said measurement side of said diaphragm is co-planar with a front surface of said frame.

4. The pressure sensor according to claim 2, wherein said sheet of material comprises a sheet of silicon material, and said signal-generating element comprises a monocrystalline piezoresistive element.

5. The pressure sensor according to claim 1, wherein said slits have a first portion that extends in a depth direction that is substantially transverse to said measuring side of said diaphragm and a second portion that extends under said rear side of said diaphragm, and one of said frame and a wall of said reference chamber has a shoulder that is closely adjacent said rear side of said diaphragm and along said outer edge of said diaphragm, with said shoulder cooperating with at least one of said rear side of said diaphragm and a rear surface of said frame to define said second portion of said slits.

6. The pressure sensor according to claim 1, wherein dimensions of said restriction are selected to provide a flow resistance that together with a volume of said reference chamber constitute a low pass filter for a pressure equalizing rate of the pressure sensor, with said low pass filter having a corner frequency that is adapted to a frequency range of dynamic pressure variations to be measured.

7. The pressure sensor according to claim 1, wherein each of said first attachment structure and said second attachment structure provides a reduced area where mechanical stresses caused by pressure are concentrated, and said first attachment structure is spaced from said second attachment structure along said outer edge of said diaphragm.

8. The pressure sensor according to claim 1, wherein said signal-generating element comprises a piezoresistive element, with said piezoresistive element being one of a bulk material element and a thin film element.

9. A photoacoustical gas detection sensor for detection and/or concentration determination of a particular gas in a surrounding environment, comprising:

a measurement chamber filled with an amount of said particular gas;

a radiation source that is spaced from said measurement chamber, with said measurement chamber having a wall area or window that is transparent to radiation of said radiation source that has a wavelength that can be one of absorbed and scattered by said particular gas; and a pressure sensor to measure absolute dynamic pressure in said measurement chamber, with said pressure sensor being one of inside said measurement chamber and adjacent said measurement chamber and including (i) a frame;

(ii) a reference chamber that is not to be exposed to the radiation of said radiation source;

(iii) a diaphragm attached to said frame, with said diaphragm including a thin planar structure having an outer edge, a measurement side facing said measurement chamber, and a rear side facing said reference chamber;

(iv) a first attachment structure interconnecting said frame and a first section of said outer edge of said diaphragm;

(v) a second attachment structure interconnecting said frame and a second section of said outer edge of said diaphragm;

(vi) a restriction that interconnects said reference chamber and said measurement chamber such that said reference chamber is in fluid communication with said measurement chamber; and (vii) a signal-generating element to detect mechanical stress in at least one of said first attachment structure and said second attachment structure, wherein at least one of said first attachment structure and said second attachment structure provides a reduced area where mechanical stresses caused by pressure are concentrated, and said signal-generating element is arranged at said reduced area, wherein sections of said outer edge of said diaphragm other than said first section and said second section are separated from said frame by slits, with a combination of said slits constituting said restriction, and wherein said reference chamber and said measurement chamber constitute a closed system filled with said particular gas.

10. The photoacoustical gas detection sensor according to claim 9, wherein said measurement chamber and said reference chamber are each formed by performing laminating and etching techniques and have substantially similar dimensions on respective sides of said frame and diaphragm.

11. The photoacoustical gas detection sensor according to claim 10, wherein a radiation reflective coating is provided on one side of said diaphragm, and a wall area of said measurement chamber that is opposite to said radiation reflective coating includes a radiation transparent area or window.

12. A method for manufacturing a pressure sensor for measuring absolute dynamic pressure, comprising:

forming at least two elongate narrow slits completely through a thin first sheet of material such that said slits define a restriction and divide said first sheet of material into
(i) a frame,
(ii) a diaphragm attached to said frame and separated from said frame by said at least two slits, with said diaphragm having an outer edge, a measurement side that is to face a surrounding environment, and a rear side,
(iii) a first attachment structure interconnecting said frame and a first section of said outer edge of said diaphragm, and
(iv) a second attachment structure interconnecting said frame and a second section of said outer edge of said diaphragm;

forming a recess in a second sheet of material;

laminating said first sheet of material to said second sheet of material such that said recess defines a reference chamber that faces said rear side of said diaphragm and is in fluid communication with said restriction, whereby said restriction places said reference chamber and the surrounding environment in fluid communication with one another when said restriction is placed in fluid communication with the surrounding environment; and providing a signal-generating element to detect mechanical stress in at least one of said first attachment structure and said second attachment structure, wherein at least one of said first attachment structure and said second attachment structure provides a reduced area which corresponds to an area of said first sheet of material that transitions from said diaphragm to said frame where mechanical stresses caused by pressure are concentrated, and the provision of said signal-generating element includes arranging said signal-generating element at said reduced area.

13. The method according to claim 12, wherein said first sheet of material and said second sheet of material each comprise a sheet of silicon material, the formation of said at least two slits in said first sheet of material comprises ionic etching said first sheet of material, and the formation of said recess in said second sheet of material comprises wet etching said second sheet of material.

14. The method according to claim 13, further comprising prior to the lamination of said first and second sheets of material, etching said second sheet of material to form a step along an upper edge of said recess such that after the lamination of said first and second sheets of material said restriction is defined by a first portion of said at least two slits that extends through said first sheet of material and a second portion that extends under said rear side of said diaphragm.

15. The method according to claim 13, further comprising depositing a thin film onto one of said first and second sheets of material by performing one of
(i) growing an oxide layer on said one of said first and second sheets of material, and
(ii) laminating a third sheet of material on said one of said first and second sheets of material, such that after the lamination of said first and second sheets, said thin film defines a material layer between said first and second sheets that has an opening that is not smaller than said diaphragm, whereby said restriction is defined by a first portion of said at least two slits that extends through said first sheet of material and a second portion that extends under said rear side of said diaphragm and is defined by said material layer and an edge of said second sheet of material that defines said recess.

16. The method according to claim 13, further comprising prior to the lamination of said first and second sheets of material, etching said first sheet of material on its rear side such that after the lamination of said first and second sheets of material said restriction is defined by a first portion of said at least two slits that extends through said first sheet of material and a second portion that extends under said rear side of said diaphragm.

17. The method according to claim 13,
wherein forming at least two elongate narrow slits completely through a thin first sheet of material comprises simultaneously forming at least two elongate narrow slits completely through each of a plurality of portions of said first sheet of material, such that said slits define in each of said plurality of portions of said first sheet of material a restriction and divide each of said plurality of portions into
(i) a frame,
(ii) a diaphragm attached to said frame and separated from said frame by said slits, with said diaphragm having an outer edge, a measurement side that is to face a surrounding environment, and a rear side,
(iii) a first attachment structure interconnecting said frame and a first section of said outer edge of said diaphragm, and
(iv) a second attachment structure interconnecting said frame and a second section of said outer edge of said diaphragm;

wherein forming a recess in a second sheet of material comprises simultaneously forming a recess in a plurality of portions of said second sheet of material, wherein laminating said first sheet of material to said second sheet of material comprises laminating said first sheet of material to said second sheet of material such that corresponding ones of said plurality of portions of said first sheet of material become bonded to corresponding ones of said plurality of portions of said second sheet of material, whereby said recess of each of said plurality of portions of said second sheet of material defines a reference chamber that faces said rear side of a corresponding said diaphragm and is in fluid communication with a corresponding said restriction, and further comprising sectioning said laminated first and second sheets of material into a plurality of individual said pressure sensors.

18. A method for manufacturing a photoacoustical gas detection sensor for detection and/or concentration determination of a particular gas in a surrounding environment, comprising:

forming at least two elongate narrow slits completely through a thin first sheet of material such that said slits define a restriction and divide said first sheet of material into
(i) a frame,
(ii) a diaphragm attached to said frame and separated from said frame by said at least two slits, with said diaphragm having an outer edge, a measurement side and a rear side, (iii) a first attachment structure interconnecting said frame and a first section of said outer edge of said diaphragm, and (iv) a second attachment structure interconnecting said frame and a second section of said outer edge of said diaphragm;

forming a first recess in a second sheet of material;

laminating said first sheet of material to said second sheet of material such that said first recess defines a measurement chamber that faces said measurement side of said diaphragm and is in fluid communication with said restriction, with said measurement chamber having a wall area or window;

forming a second recess in a third sheet of material;

laminating said third sheet of material to said first sheet of material in an atmosphere of said particular gas such that said second recess defines a reference chamber that faces said rear side of said diaphragm and is in fluid communication with said restriction, whereby said measurement chamber and said reference chamber are in fluid communication with one another via said restriction such that said particular gas is present in each of said reference chamber and said measurement chamber;

providing a radiation source that is spaced from said measurement chamber, with said radiation source to emit radiation to which said wall area or window of said measurement chamber is transparent, and with said radiation having a wavelength that can be one of absorbed and scattered by said particular gas; and providing a signal-generating element to detect mechanical stress in at least one of said first attachment structure and said second attachment structure, wherein at least one of said first attachment structure and said second attachment structure provides a reduced area where mechanical stresses caused by pressure are concentrated, and the provision of said signal-generating element includes arranging said signal-generating element at said reduced area, and wherein a combination of said frame, said reference chamber, said diaphragm, said first attachment structure, said second attachment structure, said restriction and said signal-generating element constitute a pressure sensor to measure absolute dynamic pressure in said measurement chamber.

19. The method according to claim 18, wherein said first sheet of material and said second sheet of material each comprise a sheet of silicon, said third sheet of material comprises a sheet of glass, the formation of said at least two slits in said first sheet of material comprises ionic etching said first sheet of material, the formation of said first recess in said second sheet of material comprises one of wet etching and machining said second sheet of material, and the formation of said second recess in said third sheet of material comprises one of wet etching and machining said third sheet of material.

20. The method according to claim 19, further comprising providing said second sheet of material with a through hole by one of machining and wet etching said second sheet of material, and laminating a fourth sheet of material to said second sheet of material such that said through hole is covered by said fourth sheet of material, with said fourth sheet of material being transparent to the radiation and defining said wall area or window of said measurement chamber.

21. The method according to claim 19, wherein forming at least two elongate narrow slits completely through a thin first sheet of material comprises simultaneously forming at least two elongate narrow slits completely through each of a plurality of portions of said first sheet of material, such that said slits define in each of said plurality of portions of said first sheet of material a restriction and divide each of said plurality of portions into (i) a frame, (ii) a diaphragm attached to said frame and separated from said frame by said slits, with said diaphragm having an outer edge, a measurement side and a rear side, (iii) a first attachment structure interconnecting said frame and a first section of said outer edge of said diaphragm, and (iv) a second attachment structure interconnecting said frame and a second section of said outer edge of said diaphragm;

wherein forming a first recess in a second sheet of material comprises simultaneously forming a recess in a plurality of portions of said second sheet of material, wherein forming a second recess in a third sheet of material comprises simultaneously forming a recess in a plurality of portions of said third sheet of material, wherein laminating said first sheet of material to said second sheet of material and laminating said first sheet of material to said third sheet of material comprises laminating said first sheet of material to said second sheet of material such that corresponding ones of said plurality of portions of said first sheet of material become bonded to corresponding ones of said plurality of portions of said second sheet of material while laminating said first sheet of material to said third sheet of material such that corresponding ones of said plurality of portions of said first sheet of material become bonded to corresponding ones of said plurality of portions of said third sheet of material, whereby said first recess of each of said plurality of portions of said second sheet of material defines a measurement chamber that faces said measurement side of a corresponding said diaphragm and is in fluid communication with a corresponding said restriction, and said second recess of each of said plurality of portions of said third sheet of material defines a reference chamber that faces said rear side of a corresponding said diaphragm and is in fluid communication with a corresponding said restriction and a corresponding said measurement chamber via said corresponding said restriction, and further comprising sectioning said laminated first, second and third sheets of material into a plurality of individual said photoacoustical gas detection sensors.

* * * * *